(12) United States Patent
Shnizer et al.

(10) Patent No.: US 6,372,508 B1
(45) Date of Patent: Apr. 16, 2002

(54) METHOD AND APPARATUS FOR MEASURING LIPID PEROXIDATION IN BIOLOGICAL FLUIDS AND SUSPENSIONS OF TISSUES

(75) Inventors: Sergey Shnizer, Kiriat Bialik; Abraham Resnik, Nofit; Amos Lanir, Haifa; Piuk Vladimir, Kiriat Yam, all of (IL)

(73) Assignee: Lumitest Ltd., Nesher (IL)

( * ) Notice: Subject to any disclaimer, the term of this patent is extended or adjusted under 35 U.S.C. 154(b) by 0 days.

(21) Appl. No.: 09/509,213

(22) PCT Filed: Sep. 27, 1998

(86) PCT No.: PCT/IL98/00466

§ 371 Date: May 19, 2000

§ 102(e) Date: May 19, 2000

(87) PCT Pub. No.: WO99/19728

PCT Pub. Date: Apr. 22, 1999

Related U.S. Application Data (60) Provisional application No. 60/061,464, filed on Oct. 9, 1997.

(51) Int. Cl.[7] .............................................. G01N 21/71
(52) U.S. Cl. ........................... 436/63; 436/71; 436/135; 436/172; 422/52; 422/82.08
(58) Field of Search .......................... 436/63, 71, 172, 436/135; 422/52, 82.08; 250/361 C (56) References Cited

U.S. PATENT DOCUMENTS

| | | | |
|---|---|---|---|
| 4,900,680 A | | 2/1990 | Miyazawa et al. ............. 436/71 |
| 5,061,633 A | * | 10/1991 | Meguro et al. ................ 436/71 |
| 5,513,642 A | | 5/1996 | Ostrander .................... 128/633 |
| 5,590,052 A | | 12/1996 | Kopf-Sill et al. ............ 364/498 |
| 5,726,063 A | * | 3/1998 | Gerard-Monnier et al. . 436/128 |
| 5,874,313 A | * | 2/1999 | Ahotupa ........................ 436/71 |
| 5,912,179 A | * | 6/1999 | Alvarez et al. ................ 436/63 |

FOREIGN PATENT DOCUMENTS

| | | | |
|---|---|---|---|
| DE | 4421 792 A1 | | 1/1995 |
| GB | 2279740 | * | 1/1995 |

* cited by examiner

Primary Examiner—Jeffrey Snay
(74) Attorney, Agent, or Firm—Blank Rome Comisky & McCauley LLP (57) ABSTRACT

The present invention relates to a method and apparatus for measuring the lipid peroxidation extent in biological fluids and suspensions of tissues, in which a specifically prepared lipids containing sample is exposed to heat so as to induce thermo-chemiluminescence light which is emitted by the sample and is enhanced to an amount which can be detected by a special purpose photo detector The measurement of the light allows to conclude about the content of peroxides and subsequently to obtain accurate assessment of lipid peroxidation .

11 Claims, 5 Drawing Sheets

METHOD AND APPARATUS FOR MEASURING LIPID PEROXIDATION IN BIOLOGICAL FLUIDS AND SUSPENSIONS OF TISSUES

This application is the National Stage of International Application No. PCT/IL98/00466, filed Sep. 27, 1998, which claims benefit of U.S Provisional Application No. 60/061,464, filed Oct. 9, 1997.

BACKGROUND OF THE INVENTION

1. Field of the Invention

The present invention relates to a method and apparatus for the assessment of the extent of lipid peroxidation in biological and particularly human fluids and suspensions of human tissues. It should be understood however that the present invention can be applicable also to measurement of lipid peroxidation of other substances containing lipids.

2. Description of the Prior Art

Oxygen is required for many life-sustaining metabolic reactions. Acting on an unsaturated fatty acid, active forms of oxygen (free radicals), generally produce lipid peroxides. Oxidation of the unsaturated fatty acid is accompanied by introducing oxygen molecules into double bonds. During the reaction, cis type doubles bonds sites are converted into conjugated double bonds thus producing a hydroperoxide type of lipid peroxide with a conjugated double bond.

When oxygen molecules are directly introduced into saturated or unsaturated fatty acids in a photosensitized oxidation reaction, lipid hydroperoxides with or without a conjugated double bond are generated. In decomposition and polymerization reactions, lipid hydroperoxides as a primary product derived by oxidation, produce secondary oxides of different types.

Oxygen and its activated intermediates may react with cellular components with resultant degradation or inactivation of molecules.

The set of intracellular or extracellular conditions that enable chemical or metabolic generation of reactive oxygen species such as superoxide radicals, hydrogen peroxide, lipid peroxides or related forms is known as oxidative stress. Normally, metabolic activity of the cell is able to control or prevent adverse effects of oxidative stress. The susceptibility to oxidative stress is a function of the overall balance between the factors that exert oxidative stress and those that exhibit antioxidant capability.

Free radical-induced peroxidative damage to membrane lipids has long been regarded as a critical initiating event leading to cell injury. In the presence of a free radical or a free radical initiator, biological materials, and, in particular, cell membranes which contain a relative high proportion of polyunsaturated lipids, become susceptible to oxidation.

The process of lipid peroxidation is thus associated with the loss of membrane polyunsaturated fatty acids and with the formation of hydroperoxides, free radical intermediates and other secondary products. The peroxidation of essential fatty acids may disturb the fine structure of biological membranes and may thus affect the permeability and functions of the membrane. The process of lipid peroxidation, when not aborted, may lead to the rupture of cell membranes and the release of destructive products. As a result, these processes may cause irreversible damage to the cells and may initiate and/or promote the pathogenesis at certain conditions of injury and disease.

Prevention of the potential adverse effects of oxygen and its reactive intermediates is achieved by a number of antioxidant defense systems already presented in the cells or by their enforcement from the outside by virtue of different forms of artificial antioxidants.

Hence providing for a simple, sensitive and reliable method for measuring the extent of lipid peroxidation in biological and particularly human fluids and tissues may constitute an important tool for studying various pathologies ad diseases like for example nutritional imbalance, hereditary diseases, cardiovascular diseases, cancer, diabetes adult respiratory distress syndrome (ARDS) etc.

Decomposition of the peroxides releases energy in the form of chemiluminescence. It is established fact that there is a correlation between the chemiluminescence intensity and the rate of hydroperoxide decomposition. The chemiluminescence can be triggered by heat in the thermochemiluminescence (briefly, TCL) process.

The phenomenon of TCL is mainly caused by two types of basic reactions:

I. Thermal decomposition of dioxatans-cyclic peroxides as demonstrated below:

II. Oxidation of the lipid radical during heating:

where $^1O_2$—singlet oxygen

C=O*—unstable carbonyl compound

ROO°—lipid peroxy radical

Both types of reactions exhibits the capability of lipid substances, which may be present in biological fluids and tissues to react via a free-radical oxidation chain reaction to form unstable carbonyl products.

Caused by instability of carbonyl fragments of different origins, low intensity chemiluminescence can be detected as visible light in the range 400–600 nm. Most conventional methods for measuring the lipid peroxidation extent, for example the popular TBA-RS lipid peroxidation test do not rely on chemiluminescence.

In the method described in the U.S. Pat. No. 4,900,680 to Miyazawa et al a sample containing lipids is subjected to a lipid chromatography to separate the lipids into lipid classes, subsequently brought into contact with a luminescent reagent to generate light in an amount corresponding to the content of the lipid hydroperoxide.

The most relevant to the present invention known method is method and apparatus for the measurement of luminescence of biological fluids as described in DE laid open publication No.4421792 to Shnizer et al. herein incorporated by reference. In this document there is described a method for the preparation of a sample of biological fluid which comprises heating the sample under vacuum at a temperature, which is in the range between the freezing point of the sample and the temperature sufficient to induce luminescence emitted by the tested fluid.

Unfortunately the known method does not allow to measure intensity of luminescence in a reliable manner and to establish stable correlation between the intensity of TCL and time. The reason for this lies in the fact that the structure of frozen sample is not continuous and contains voids associated with evacuation of liquid phase. The other reason is relatively slow heating of the sample which did not left enough time for measuring of the TCL.

It can be readily appreciated that the problem of reliable measuring of extent of LPX still needs a solution.

SUMMARY OF THE INVENTION

The main object of the present invention is to provide for a method and apparatus for measuring of TCL in which the above mentioned desiderata are sufficiently reduced or overcome.

In particular the main object of the present invention is to provide for a new and improved method and apparatus for measuring the lipid peroxidation extent enabling reliable measuring of TCL and establishing of stable correlation between the intensity of TCL and time.

The above and other objects and advantages of the present invention can be achieved in accordance with the following combination of its essential features, referring to different embodiments thereof.

In an embodiment of the present invention referring to a method of measuring lipid peroxidation in biological fluids, in suspensions of biological tissues or the like, wherein a sample of said fluid or suspension is heated so as to induce therein thermochemical luminescence (TCL) and amount of said TCL can be measured, said method comprising the following sequence of steps:

a) bringing a sample of said fluid or suspension in a receptacle having substantially flat bottom
b) placing said receptacle within a sublimation chamber and putting thereof on a substrate made of substantially metallic material
c) imparting reciprocating motion to said receptacle so as to distribute said sample over the bottom of said receptacle in a substantially homogeneous manner
d) subjecting of said sample residing within said chamber to sublimation at reduced pressure during period of time sufficient for evacuation from said sample of a liquid phase and formation on the bottom of said receptacle of a substantially continuous film consisting of dry solid residual
e) bringing said receptacle with said residual in a processing chamber and placement thereof on a plate having temperature sufficient for inducing TCL and emitting thereof by said residual
f) sensing said TCL and measuring the intensity thereof for example by optical photo-detector during period of time sufficient for establishing stable correlation between TCL intensity and time.

In accordance with one of the preferred embodiments referring to method said receptacle is formed as disposable vessel made of thin metallic foil and said plate is made of aluminum.

As per another preferred embodiment said reciprocating motion is imparted to said sample during at least 40 sec so as to distribute said sample over the bottom of said receptacle as a layer with thickness 0.3–0.5 mm.

According to other preferred embodiment said sublimating step is carried out at reduced pressure not exceeding 2 mbar and during period of time not exceeding 10 min.

In still further preferred embodiment before placement said receptacle onto said plate it is heated up to at least 60 deg. C.

And in yet another preferred embodiment relating to method said TCL intensity is measured in the range of 400–600 nm during at least 300 sec.

According to the first preferred embodiment referring to an apparatus for measuring lipid peroxidation in biological fluids in suspensions of biological tissues or the like, wherein a sample of said fluid or suspension is heated so as to induce therein thermochemical luminescence (TCL) and amount of said TCL can be measured, said apparatus comprising:

a) sublimation chamber provided with a means for homogeneous distributing of said sample within a receptacle and with a sublimating means capable to evacuate liquid phase from said sample so as to form a thin substantially continuous film consisting of dry solid residual, said means for homogeneous distributing comprises a substrate made of preferably metallic material, said substrate is provided with a depression for receiving said receptacle therein and there is provided a driving means for imparting reciprocating motion to said substrate
b) heating chamber provided with a plate for placing said receptacle thereon, with a heating means for heating said plate and with a means for detection and measuring said CTL
c) data recording unit for presentation in visual manner results of measuring of said TCL
d) control and data processing unit for controlling said means for homogeneous distributing, said driving means, said sublimating means, said heating means, said means for detection and measuring said TCL and said data recording unit.

According to one of the preferred embodiments of the apparatus said sublimating means comprises vacuum pump capable to generate reduced pressure within said sublimation chamber.

In accordance with the other preferred embodiment said substrate is formed as a disc made of aluminum, said disc is supported by elastic tubular elements connecting said disc with the basis of said sublimating chamber and said driving means comprises a motor imparting reciprocating motion to said plate via a cam.

And as per still further preferred embodiment of the apparatus said heating means comprises transistor and temperature sensor and said means for detection and measuring TCL comprises photo-electronic multiplier.

The present invention in its various embodiments has only been summarized briefly. For better understanding of the present invention as well of its advantages, reference will now be made to the following description of its embodiments.

BRIEF DESCRIPTION OF THE DRAWINGS

FIGS. 1a,b show schematically an apparatus for measuring the lipid peroxidation extent in accordance with the present invention and a receptacle for retaining the sample of biological fluid;

FIGS. 5a,b show two curves depicting correlation between TCL intensity and time established by the method in accordance with the present invention.

DETAILED DESCRIPTION OF THE PREFERRED EMBODIMENTS

With reference to FIG. 1a an apparatus for measuring TCL in accordance with the present invention comprises sample preparation unit 1 and measuring unit 2.

Referring to FIG. 1b, a small amount, typically 150 ml, of a sample of a biological fluid to be tested on lipid peroxidation content, is placed in a receptacle 3, formed preferably as disposable cuvette having flat bottom of a typical diameter 5 cm.

Figure 2A:
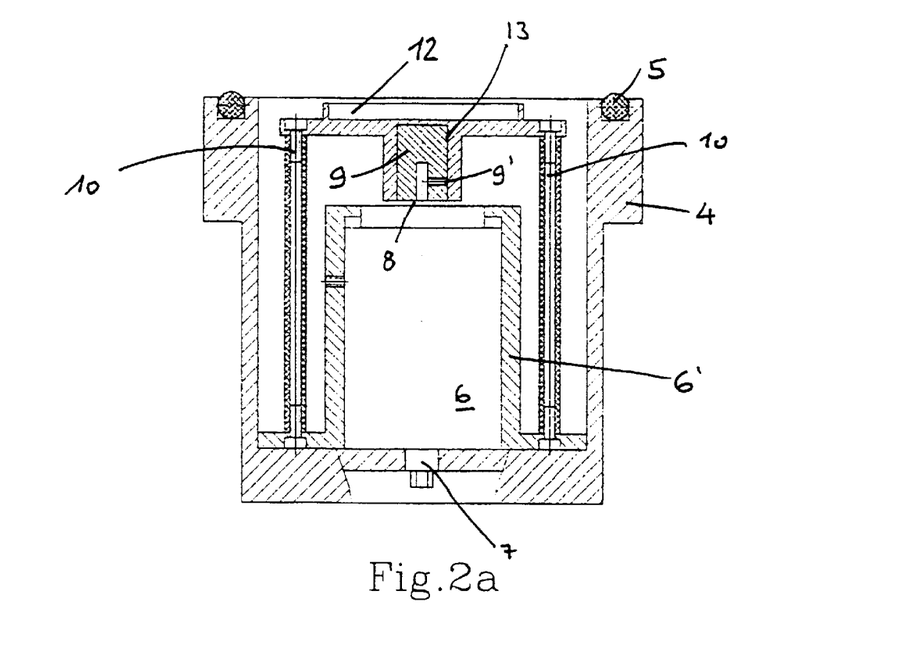
FIGS. 2a,b show respectively longitudinal crossection and partially sectioned top view of the sublimation chamber.
Figure 2B:
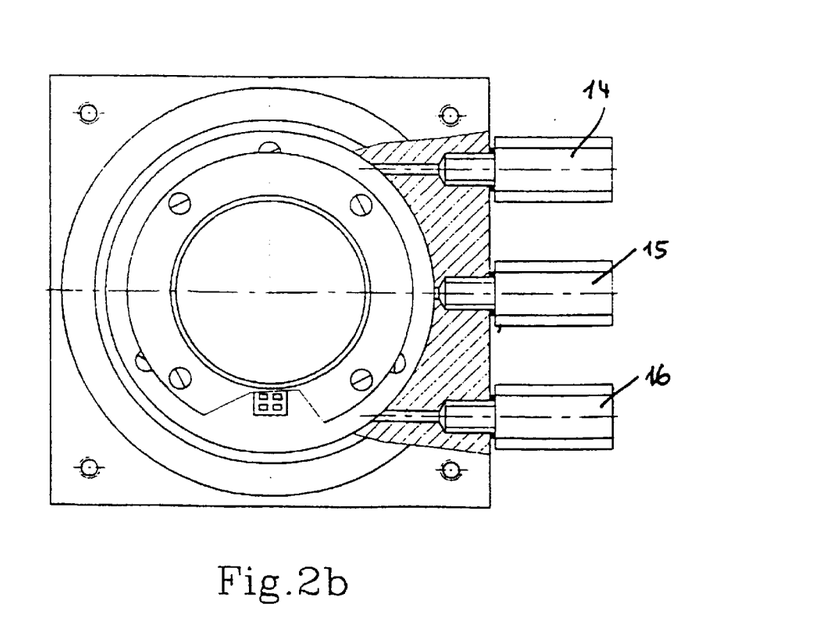
Figure 3:
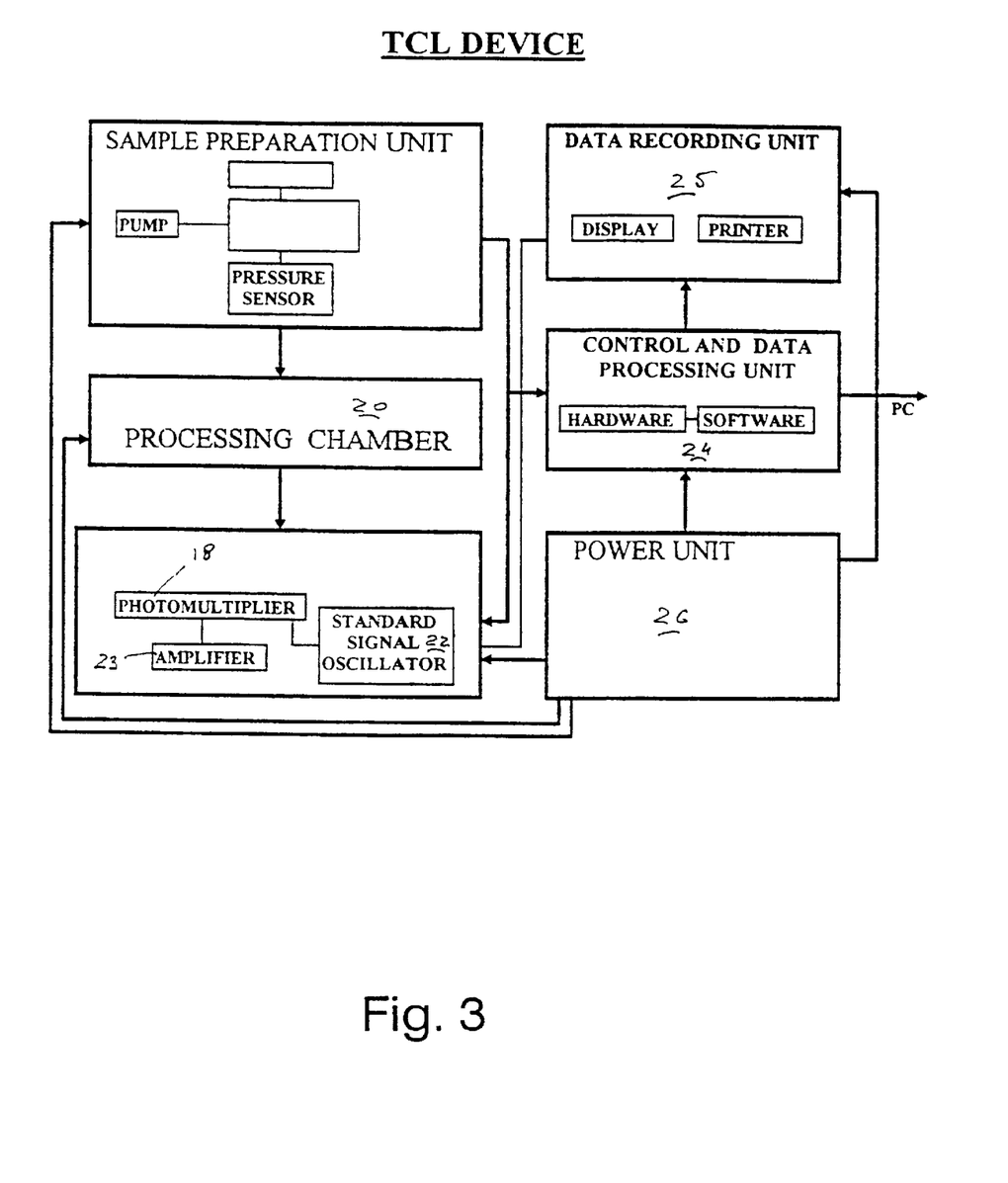
FIG. 3 is a flow chart diagram of the method for measuring the lipid peroxidation extent according to the present invention.

The aforesaid cuvette containing a liquid sample is brought into the sample preparation unit, which is formed as cylindrical sublimation chamber 4, which by virtue of an O-ring sealing 5 can be tightly closed by a covering (not shown) so as to keep the chamber's interior sealed from the outside.

Within the chamber there is provided a motor 6 rigidly mounted on the chamber's base by virtue of bracket 6'. The motor is energized via electrical wiring going through opening 7 made in the chamber's' base. The motor' shaft 8 carries cam 9 rigidly connected thereto by virtue of fixation screw 9'. Resting on supporting elements 10 there is provided substantially flat plate 11 formed on its upper side with depression 12 for receiving therein receptacle 3. The lower side of the plate is provided with cylindrical hole 13 which diameter is chosen in such a manner that it enables entering the cam in the hole and thus imparting reciprocating motion to the plate when the motors rotates the cam.

Supporting elements 10 are formed as thin tubes made of elastic material so as to allow substantially flat reciprocating motion of the plate when it is driven by a cam. The receptacle with a sample of biological fluid is put in the depression 12 of the plate and the motor is activated so as to impart reciprocating motion to the plate and thus shaking of the sample. The frequency and duration of the shaking action is chosen so as to reach basically uniform distribution of the sample liquid layer over the bottom of the receptacle. In practice the shaking procedure should be carried out during 40–60 sec so as to obtain after shaking the sample layer with thickness 0.3–0.5 mm.

The aforesaid experimentally determined thickness of the sample liquid layer is essential to avoid undesirable formation of bubbles of the sample liquid and their influence on the desiccation (sublimation) step which is carried out after shaking and is described in more details below.

If the shaking step is properly carried out it is possible to achieve after the forthcoming sublimation step the dry residual (sublimate) in the form of a thin continuous film which is uniformly distributed over the receptacle's bottom.

The desiccation (sublimation) process is carried out inside the sublimation chamber at reduced pressure which is created and maintained by virtue of a vacuum pump (not shown) communicating with the interior of the chamber via port 14. Communicating with the chamber's interior via port 15 an appropriate vacuum sensing means is also provided for measuring the current pressure within the sublimation chamber. It has been empirically found that there should be a balance between the reasonable duration of the desiccation process required for establishing reduced pressure and the desirable properties of the desiccated residue enabling reliable measurement of the TCL. These properties include the amount of dry substance in the residual thin film, which should be at least 99.9% and the absence of voids associated with bubbling of the fluid during sublimation.

It has been empirically found that the best results in terms of short term of the desiccation process and achievable properties of the desiccated sample enabling most reliable measurement of the TCL are obtained if the chamber is vacuumized for 1–3 min so as to reduce the pressure up to at least 2 mbar and if this pressure is maintained for at least 6–8 min. For this purpose mechanical vacuum pump with pumping speed of 20 l/min and ultimate pressure of $1 \times 10^{-3}$ torr can be advantageously employed.

To avoid freezing of the desiccated sample as a result of high desiccation rate the plate 11 is made of material having high thermal conductivity, for example metallic material. It can be readily appreciated that when the receptacle with the sample is put into depression 12 of the plate there is established thermal contact therebetween and by virtue of high thermal conductivity of the plate there is no freezing of the sample during desiccation. In practice it is advantageous to manufacture the plate from aluminum, which combines good thermal conductivity and good machinability. However other metallic or non metallic materials can be used as well, providing that their thermal conductivity, machinability and cost are comparable with those of Aluminum.

After completing the desiccation process the vacuum pump is turned off and the chamber is connected with the ambient atmosphere by virtue of port 16 so as to return the pressure within the chamber to a normal one.

The cover is opened and receptacle with the desiccated sample is transferred from the sample preparation unit 1 into processing chamber 20 of measuring unit 2 in which the TCL is measured.

The processing chamber is provided with a plate 17 for placing the receptacle with frozen sample beneath a photo-detector means 18 with heating, means 19 for heating the plate and with sensing means 21 for measuring the temperature of the plate.

In contrast to the known in the art methods in which the frozen sample residing on the plate should be heated together therewith to provoke the TCL, in the present invention the sample is put on the already heated plate which was heated up to certain temperature before putting the receptacle thereon.

It has been established that it is very advantageous to employ as a heating means a powerful transistor. The temperature of the transistor is regulated by a temperature sensor attached to the transistor body. Due to fast response time of the transistor, stable temperature regime is maintained which is crucial for adequate luminescence measurements. In practice the plate should be heated up to app. 60 deg. C. before the receptacle is brought into processing chamber and put on the plate.

Analysis of the sample is carried out by a photo-detector means 18, for example by conventional Photo-Multiplier, capable to measure intensity of the TCL in the visible range of 300–650 nm.

Calibration signal generated by a high frequency diode standard signal oscillator 22 is measured both before and after measurement of TCL emission of the sample and is multiplied by an amplifier 23.

The signal output from the anode of the multiplier is amplified and passed to the computer, which operates as a data-acquisition terminal, simultaneously recording the time and the intensity of the emitted luminescence light. The TCL curve obtained is treated mathematically, while two main parameters are provided for treatment; 1) TCL amplitude and 2) slope of the TCL curve, measured between 120 and 140 sec after the receptacle with the sample is put on the heated plate. The measurement is terminated after this period of time. Processing and mathematical treatment of the analysis results is carried out by a generally known method of signal processing within control and data processing unit 24.

Results of measurements of TCL intensity versus time are displayed on the computer screen and/or printer of the data recording unit 25. Power unit 26 is provided for supplying electrical energy required for energizing the apparatus.

Now with reference to FIGS. 4–5a,b and non limiting examples below it will be shown how measuring of TCL in accordance with the present invention can be carried out and how results of these measurements can be advantageously used in practice in comparison with the prior art method.

Figure 4:
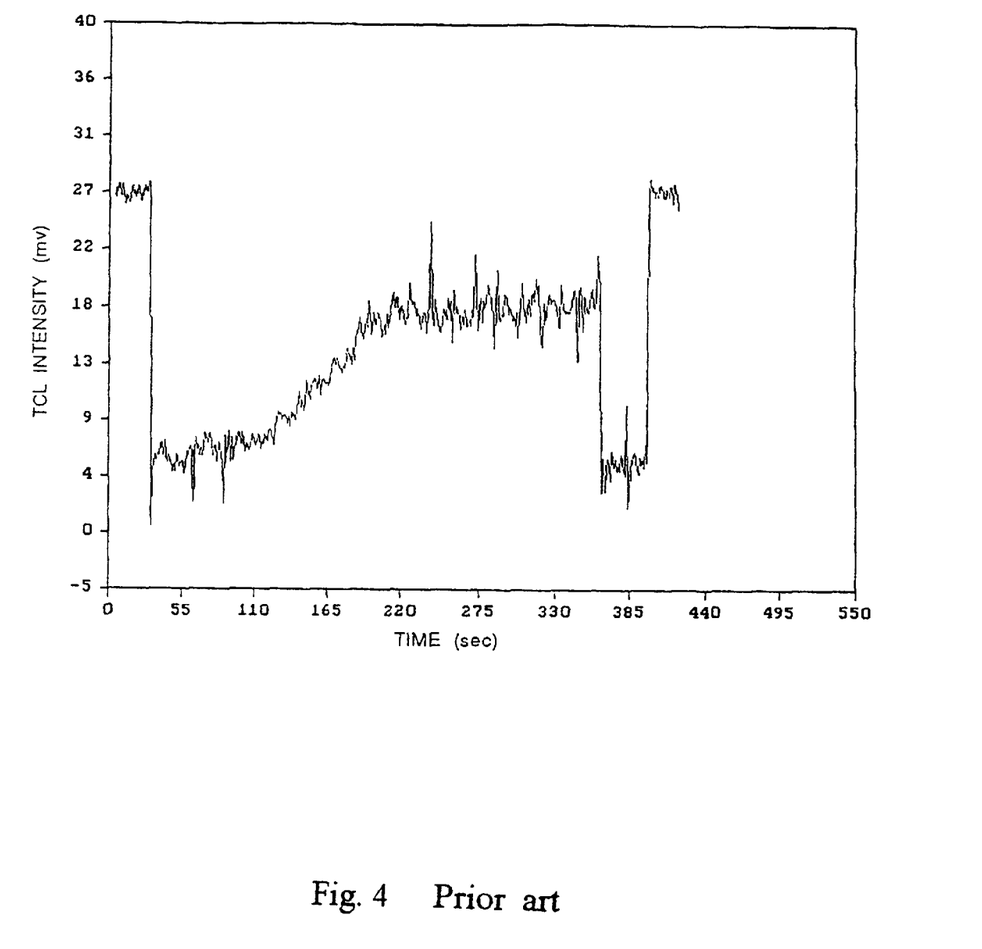
FIG. 4 is a graph showing a correlation between TCL intensity and time obtained according to the prior art method.
Figure 5:
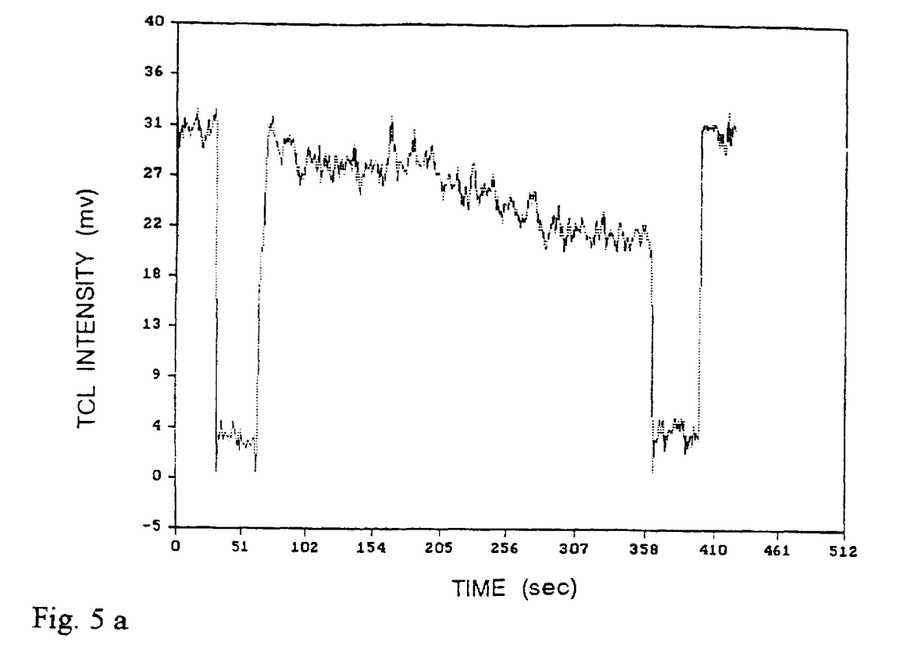

In FIG. 4 there is presented typical dependence of TCL intensity on time measured in accordance with the prior art method in which the sublimated sample is heated simultaneously with the plate. It can be readily appreciated that this dependence does not have monotone character and consists of two sections. The first, ascending section is associated with heating of the sample and corresponds to intiation of luminescence.

The second section is associated with more or less established amount of luminescence emitted by the sample. According to the shape of this section it is difficult to conclude about the rate of luminescence, seeing that the TCL intensity does not change significantly with time and therefore it is not possible to predict unequivocally the tendency of this dependence.

In the non limiting example 1 below there is described how TCL measurement in accordance with the present invention was used for measuring the lipid peroxidation extent for patients with acute respiratory distress syndrome.

EXAMPLE 1

12 samples of bronchoalveolar lavage fluid (BALF) from patients with acute respiratory distress syndrome (ARDS) have been tested.

All patients suffered from severe lung malfunction as reflected by lung injury scores greater than 2.5, and were mechanically ventilated with positive pressure ventilation. The control group consisted of 6 patients with normal respiratory activities. Patients were delivered to the post-operational block after extensive cavity treatment and were extubated 2 to 4 hours later. The TCL analysis has been performed before the extubation.

Cuvette with 150 microliters of BALF was brought into sublimation chamber of the apparatus, put on the plate and horizontally shaked for 40 sec so as to distribute the sample homogeneously over the bottom of the cuvette. Then the chamber was evacuated so as to reduce the pressure therein up to 2 mbar. This pressure was maintained for 6–8 min until rather thin continuous film of dry residual of BALF having 0.3 mm thickness is formed on the cuvette's bottom. The cuvette is brought into measuring chamber and put on the heating plate which has been heated beforehand up to 80deg. C.

The measurement of TCL was conducted by commercially available photo-multiplier. Results of measurement are shown in FIGS. 5a,b.

The BALF TCL of patients in the control group (FIG. 5a) was characterized by a descending intensity of TCL defined by a negative slope. The TCL kinetic curve of patients with ARDS (FIG. 5b) was characterized by immediate increase of intensity of TCL defined by a very definite positive slope. It has been found an avalanche-like increase in TCL intensity associated with high lipid peroxidation (LPx) state in BALF for ARDS patients.

The above described method of measurement of TCL and apparatus for its implementation is very useful for practical use in measuring active reactive carbonyls as products of LPx. Data are obtained fast within short sample preparation procedure and enable reliable prediction of TCL intensity as function of time and thus more valuable diagnostics of possible reasons associated with LPx.

The present invention can be used in various fields where assessment of LPx is required, and is carried out by measuring of TCL, for example assessment of specific diseases caused by nutritional imbalance, environmental exposure hereditary diseases, cancer, liver damage, diabetes, renal failure, infertility, assessment of activity of new forms of antioxidants, assessment of resistance of new medical substances to oxidation etc.

We claim:

1. A method of measuring lipid peroxidation in a biological sample, in which the sample is heated to induce therein thermochemical luminescence (TCL) and in which said TCL is measured, said method comprising the steps of:
    a) providing a receptacle having a substantially flat bottom for receiving said sample;
    b) introducing said the sample into said receptacle;
    c) bringing said receptacle into contact with a heat sink member, said heat sink member is made of material having high thermal conductivity;
    d) imparting motion to said receptacle to distribute said sample over the bottom of said receptacle in a substantially homogeneous manner;
    e) drying said sample without causing freezing thereof by subjecting said sample to a reduced pressure and without adding heat for a period of time sufficient to remove the liquid from the sample and form a continuous layer of dry solid;
    f) heating said dry solid layer to a temperature sufficient for inducing TCL therein; and
    g) sensing said TCL and measuring thereof for a period of time sufficient for establishing a stable correlation between TCL intensity and time.

2. A method as defined in claim 1, in which said receptacle comprises a disposable vessel made of thin aluminum foil and said heat sink member is an aluminum plate.

3. A method as defined in claim 1, in which a reciprocating motion is imparted to said receptacle for at least 40 seconds to form a continuous layer having thickness 0.3–0.5 mm.

4. A method as defined in claim 1, in which said reduced pressure does not exceed 2 mbar and said drying time does not exceed 10 minutes.

5. A method as defined in claim 1, in which heating said dry solid is carried out at a temperature of at least 60° C.

6. A method as defined in claim 1, in which measuring of said TCL is carried out by measuring the intensity thereof in the range of 400–600 nm for at least 300 seconds.

7. An apparatus for measuring lipid peroxidation in a biological sample in which the sample is heated so as to induce therein thermochemical luminescence (TCL) and said TCL is measured, said apparatus comprising:
    a drying chamber for receiving a receptacle with the sample introduced therein, said drying chamber is in communication with an evacuating means for evacuating liquid from the sample without freezing thereof and without adding heat to the sample, said drying chamber comprises
        i) a heat sink member made of a high thermal conductivity material, and
        ii) driving means for imparting motion to said receptacle;

a heating chamber provided with a means for heating said receptacle and a means for measuring the TCL of said dried sample;

a data presentation unit for presenting the TCL measurements; and a control and date processing unit for controlling the driving means, the evacuating means, the heating means, the means for measuring the TCL and the data presentation unit.

8. The apparatus as defined in claim 7, in which said receptacle comprises a disposable vessel made of aluminum foil, and said heat sink member comprises an aluminum plate, said plate having a depression for receiving the receptacle therein.

9. The apparatus as defined in claim 7, in which said evacuating means comprises a vacuum pump for generating reduced pressure within the drying chamber.

10. The apparatus as defined in claim 8, in which said plate is supported by elastic tubular elements connecting said plate with the bottom of the drying chamber, and said driving means comprises a motor and a cam.

11. The apparatus as defined in claim 7, in which said heating means comprises transistor and temperature sensor and said means for measuring of the TCL comprises photo-electronic multiplier.

* * * * *